United States Patent
Ingram et al.

(10) Patent No.: US 10,668,263 B2
(45) Date of Patent: Jun. 2, 2020

(54) VENTED CONNECTOR FOR MEDICAL FLUID VESSELS

(71) Applicant: NEOMED, INC., Woodstock, GA (US)

(72) Inventors: Aaron N. Ingram, Canton, GA (US); Benjamin Martin Davis, Woodstock, GA (US); Mark M. Costello, County Mayo (IE); Tony Doherty, County Mayo (IE); John Burke, County Roscommon (IE)

(73) Assignee: NeoMed, Inc., Woodstock, GA (US)

( * ) Notice: Subject to any disclaimer, the term of this patent is extended or adjusted under 35 U.S.C. 154(b) by 71 days.

(21) Appl. No.: 14/844,956

(22) Filed: Sep. 3, 2015

(65) Prior Publication Data
US 2016/0067471 A1 Mar. 10, 2016

Related U.S. Application Data

(60) Provisional application No. 62/192,614, filed on Jul. 15, 2015, provisional application No. 62/047,389, filed on Sep. 8, 2014.

(51) Int. Cl.
*A61M 39/10* (2006.01)
*A61J 1/14* (2006.01)
*A61M 39/20* (2006.01)

(52) U.S. Cl.
CPC ............ *A61M 39/10* (2013.01); *A61J 1/1412* (2013.01); *A61M 39/20* (2013.01); *A61M 2039/205* (2013.01)

(58) Field of Classification Search
CPC .. A61M 39/10; A61M 39/1011; A61M 39/20; A61M 25/04; A61M 2039/205;
(Continued)

(56) References Cited

U.S. PATENT DOCUMENTS 4,237,935 A   12/1980   Delmonte et al.
4,416,273 A   11/1983   Grimes
(Continued)

FOREIGN PATENT DOCUMENTS

CA   2167572 A1   2/1995
CA   2379187 A1   2/2001
(Continued)

OTHER PUBLICATIONS

English Translation of Japanese Office Action for JP Ap. No. 2017-531979; dated Mar. 27, 2018; 4 pgs.
(Continued)

*Primary Examiner* — Kevin C Sirmons
*Assistant Examiner* — Tezita Z Watts
(74) *Attorney, Agent, or Firm* — Dority & Manning, P.A.

(57) ABSTRACT

A connector for medical fluid vessels includes a fluid-seal fitting such as a male plug defining a lumen and mating with a cooperating connector, a mechanical fastener such as a screw thread for mating with the cooperating connector, and an outer housing positioned around the plug to form an annular space. Optionally, a cap can be provided with a fluid-seal fitting such as a male plug for mating with the lumen of the connector. The connector includes one or more vent openings for drainage and air-drying of any residual fluid in the annular space when capped, as well as for breaking a vacuum to prevent fluid backflow and thus ensure more accurate dosing. In some embodiments, the vent openings are provided in the outer housing. And in some embodiments, the vent openings are provided in the cap.

17 Claims, 6 Drawing Sheets

(58) Field of Classification Search
CPC .. A61M 2039/1083; A61M 2039/1088; A61M 2039/0036; A61M 2039/266; A61J 1/1412
See application file for complete search history.

(56) References Cited

U.S. PATENT DOCUMENTS

| | | | |
|---|---|---|---|
| 4,904,238 A | 2/1990 | Williams | |
| 4,994,068 A | 2/1991 | Hufnagle | |
| 5,385,372 A | 1/1995 | Utterberg | |
| 5,401,255 A * | 3/1995 | Sutherland | A61M 39/24 604/247 |
| 5,591,344 A | 1/1997 | Kenley et al. | |
| 5,881,774 A | 3/1999 | Utterberg | |
| 5,951,519 A | 9/1999 | Utterberg | |
| D463,546 S | 9/2002 | Jansen et al. | |
| 6,447,480 B1 | 9/2002 | Brunel | |
| D473,646 S | 4/2003 | Baillargeon et al. | |
| 6,883,778 B1 * | 4/2005 | Newton | A61M 39/26 251/149.1 |
| 7,077,829 B2 | 7/2006 | McGuckin, Jr. et al. | |
| 7,628,782 B2 | 12/2009 | Adair et al. | |
| 7,658,734 B2 | 2/2010 | Adair et al. | |
| 7,686,823 B2 | 3/2010 | Pingleton et al. | |
| 7,988,683 B2 | 8/2011 | Adair et al. | |
| 8,066,670 B2 | 11/2011 | Cluff et al. | |
| D665,497 S | 8/2012 | Marshall et al. | |
| 8,333,693 B2 | 12/2012 | Hamazaki | |
| 8,491,535 B2 | 7/2013 | Limaye | |
| 8,506,549 B2 | 8/2013 | Breuer-Thal et al. | |
| 8,932,264 B2 | 1/2015 | DeSalvo | |
| D736,906 S | 8/2015 | Schultz | |
| D737,436 S | 8/2015 | Lev et al. | |
| 9,308,362 B2 | 4/2016 | Mansour et al. | |
| 9,814,871 B2 | 11/2017 | Wlodarczyk et al. | |
| 2002/0173748 A1 | 11/2002 | McConnell et al. | |
| 2003/0032940 A1 * | 2/2003 | Doyle | A61M 39/045 604/533 |
| 2004/0238776 A1 | 12/2004 | Peters et al. | |
| 2005/0124935 A1 | 6/2005 | McMichael | |
| 2006/0161115 A1 * | 7/2006 | Fangrow | A61M 39/26 604/249 |
| 2008/0128646 A1 | 6/2008 | Clawson | |
| 2008/0183153 A1 | 7/2008 | Enns | |
| 2008/0200904 A1 * | 8/2008 | Cluff | A61M 25/00 604/537 |
| 2010/0292673 A1 | 11/2010 | Korogi et al. | |
| 2011/0044850 A1 * | 2/2011 | Solomon | A61M 39/162 422/28 |
| 2011/0240162 A1 | 10/2011 | Zeyfang | |
| 2012/0022457 A1 * | 1/2012 | Silver | A61M 39/1011 604/187 |
| 2012/0029481 A1 * | 2/2012 | Pech | A61M 39/10 604/533 |
| 2012/0323221 A1 | 12/2012 | Gallo et al. | |
| 2013/0079730 A1 | 3/2013 | Mosler et al. | |
| 2013/0103002 A1 | 4/2013 | Fruenlund et al. | |
| 2014/0276458 A1 | 9/2014 | Mansour et al. | |
| 2015/0005716 A1 | 1/2015 | Adair et al. | |

FOREIGN PATENT DOCUMENTS

| | | |
|---|---|---|
| EP | 2583715 A1 | 4/2013 |
| GB | 2453361 A | 4/2009 |
| JP | A09000618 | 9/1997 |
| JP | 2008518719 A | 6/2008 |
| WO | 2006052655 A2 | 5/2006 |

OTHER PUBLICATIONS

Examiner's Report for CA 2,959,393; dated Jun. 4, 2018; 4 pgs.
ISO 80369-3, Small Bore Enteral Connector Standards; 3 pgs; Jul. 21, 2014.
ENFit Female Connector; 1 pg; date unknown.
ENFit Male Connector; 1 pg; date unknown.
New ISO Tubing Connector Standards: A Follow-Up to the Sentinel Event Alert Webinar PowerPoint Presention; www.jointcommission.org; 50 pgs; Dec. 3, 2014.
New Tube Feeding Connectors Webinar PowerPoint Presention; www.oley.org; 24 pgs; Jun. 24, 2014.
StayConnected2014 Informational Bracelet; 1 pg; date unknown. http://www.stayconnected2014.org/get-ready.html; 1 pg; date unknown.
International Search Report & Written Opinion for PCT/US2015/048382; dated Nov. 5, 2015; 11 pgs.

* cited by examiner

VENTED CONNECTOR FOR MEDICAL FLUID VESSELS

CROSS-REFERENCE TO RELATED APPLICATIONS

This application claims the priority benefit of U.S. Provisional Patent Application Ser. No. 62/047,389 filed Sep. 8, 2014, and U.S. Provisional Patent Application Ser. No. 62/192,614 filed Jul. 15, 2015, the entireties of which are hereby incorporated herein by reference for all purposes.

TECHNICAL FIELD

The present invention relates generally to medical devices, and more particularly to connectors for vessels for fluids in the medical field.

BACKGROUND

Healthcare patients are commonly given fluids such as medication and nutrients by being connected to fluid-delivery systems via fluid vessels. Common fluid vessels for delivering such fluids include small-bore tubes and catheters. A problem arises when these fluid tubes are misconnected. That is, when a tube from one fluid delivery system is connected to a tube intended for connection to another fluid delivery system that serves a completely different function, for example, when a feeding administration set is inadvertently connected to a tracheostomy tube. Such tubing misconnections are also referred to as LUER misconnections, small-bore misconnections, and/or wrong-route errors. Tubing misconnections have resulted in patient injuries and/or deaths, and are widely recognized as underreported.

An underlying cause of these misconnections has been attributed to the universal design of LUER connectors, which are one of the most commonly used types of small-bore connectors in healthcare. These connectors are used to couple the tubing of one medical device to another. However, the simple design and ease of use of LUER connectors allows the tube of the device of one delivery system to be connected to a tube of an unrelated system that has a different intended use (e.g., vascular, enteral, respiratory, epidural, or intrathecal), resulting in healthcare providers inadvertently connecting wrong systems together and thereby causing liquids (e.g., medications or enteral feedings) or gases (e.g., oxygen) to be delivered through the wrong route.

Efforts are underway to develop standards, such as the ISO 80369 standards, for tubing connections. These standards hold the promise of significantly addressing the tubing-misconnection problem. For example, these standards provide for a new connector for enteral feeding tubes that prevents misconnection to non-enteral connectors. This new enteral-only tube connector is also referred to as the ENFIT connector.

Yet there remain other opportunities for improving these and other connectors. For example, the new ENFIT connector for enteral feeding tubes includes an outer housing that could retain feeding liquids and thereby allow for bacteria colonization. This can result in unsanitary conditions that can inadvertently contaminate feeding fluids later delivered to the patient through the degraded ENFIT connector.

Accordingly, it can be seen that needs exist for improved connectors for fluid tubes to reduce the risk of bacteria colonization. It is to the provision of solutions to this and other needs that the present invention is primarily directed.

SUMMARY

In example embodiments, the present invention relates to individual connectors as well as connector-sets (of individual connectors) for coupling together two medical-fluid vessels. The connectors and connector-sets advantageously provide for drainage and air-drying of any residual fluid that might otherwise be retained and result in bacteria colonization, as well as for breaking a vacuum to prevent fluid backflow and thus ensure more accurate dosing.

In one aspect, the present invention relates to a connector that includes a fluid-seal fitting such as a male plug for mating with a cooperating connector, a mechanical fastener such as a screw thread for mating with the cooperating connector, and an outer housing positioned around the plug to form an annular space. The connector outer housing includes one or more vent openings for drainage and air-drying of any residual fluid in the annular space when the cap is plugged on. For example, the connector vent openings can be in an endwall of the outer housing, a peripheral sidewall of the outer housing, or both.

In another aspect, the invention relates to a sanitary cap that includes a fluid-seal fitting such as a male plug for mating with a lumen of the connector plug. The cap includes one or more vent openings for drainage and air-drying of any residual fluid in the annular space when the cap is plugged on. For example, the cap vent openings can be in an endwall body of the cap, a peripheral sidewall of the cap, or both. In some embodiments in which the cap vent openings are in the cap sidewall, they are formed by notches or recesses between segments of the cap sidewall, and in these or other similar embodiments mechanical stop surfaces are provided on the cap and the connector to limit to travel of the cap sidewall relative to the outer-housing sidewall to ensure that the cap vents remain open for ventilation.

These and other aspects, features, and advantages of the invention will be understood with reference to the drawing figures and detailed description herein, and will be realized by means of the various elements and combinations particularly pointed out in the appended claims. It is to be understood that both the foregoing general summary description and the following brief description of the drawings and detailed description of example embodiments are exemplary and explanatory of preferred embodiments of the invention, and are not restrictive of the invention, as claimed.

DETAILED DESCRIPTION OF EXAMPLE EMBODIMENTS

Figure 1:
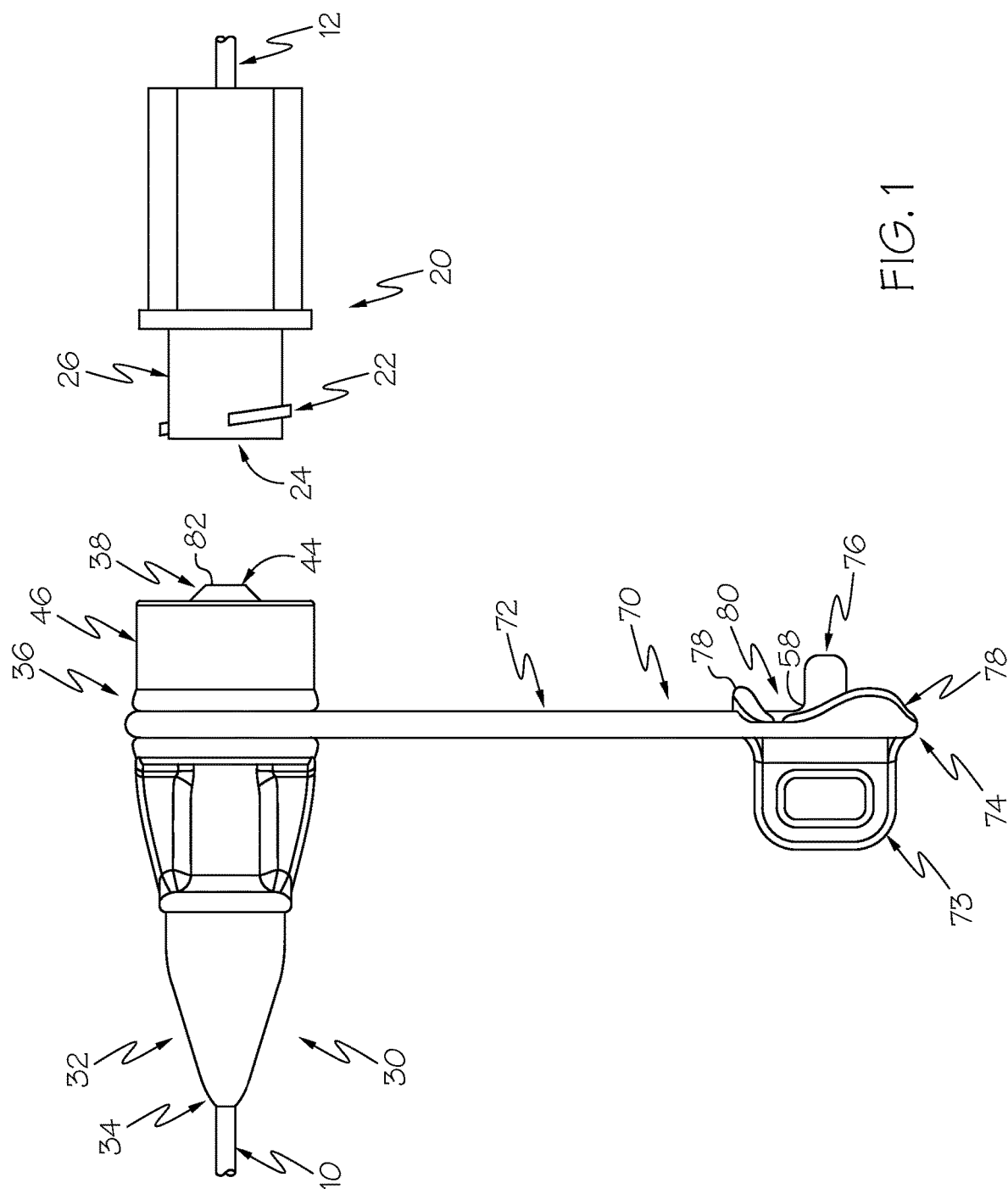
FIG. 1 is a side view of a vented male connector according to a first example embodiment of the present invention, shown with a mating female connector and with its cap unplugged so that it's ready for connection to the mating female connector.
Figure 3:
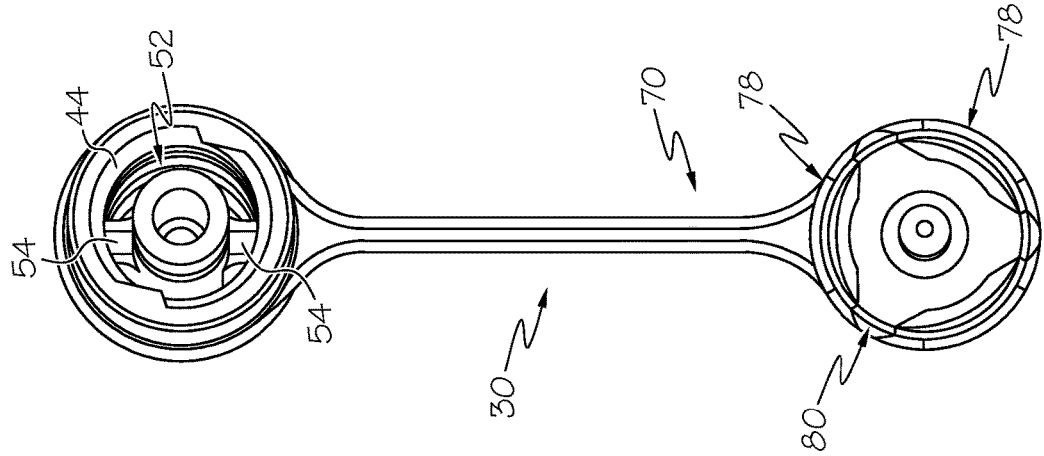
FIG. 3 is another front perspective view of the male connector of FIG. 1.
Figure 2:
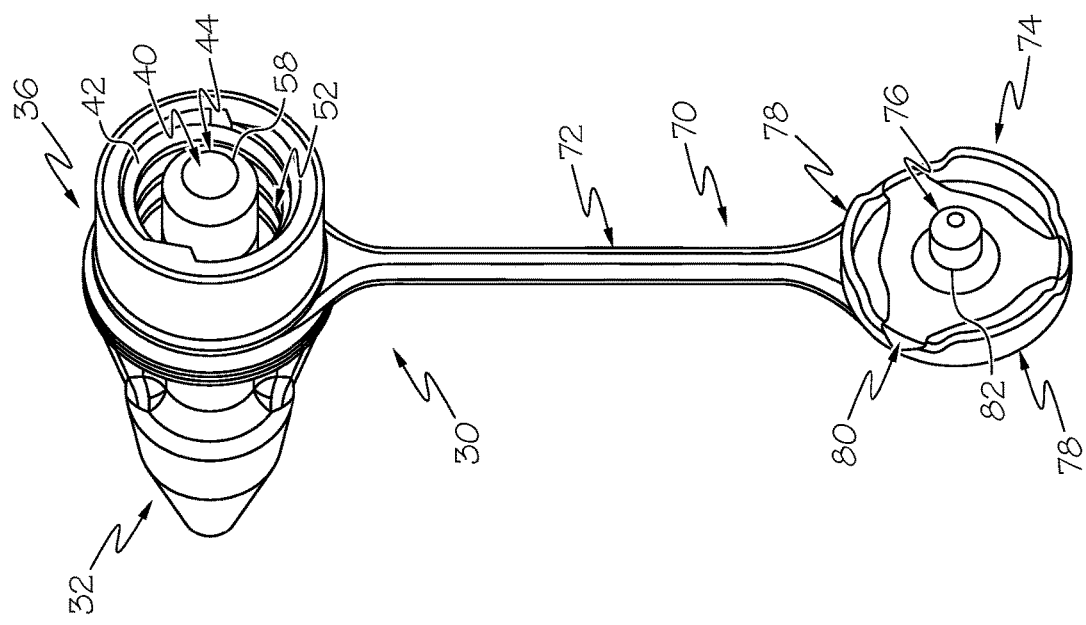
FIG. 2 is a front perspective view of the male connector of FIG. 1.
Figure 5:
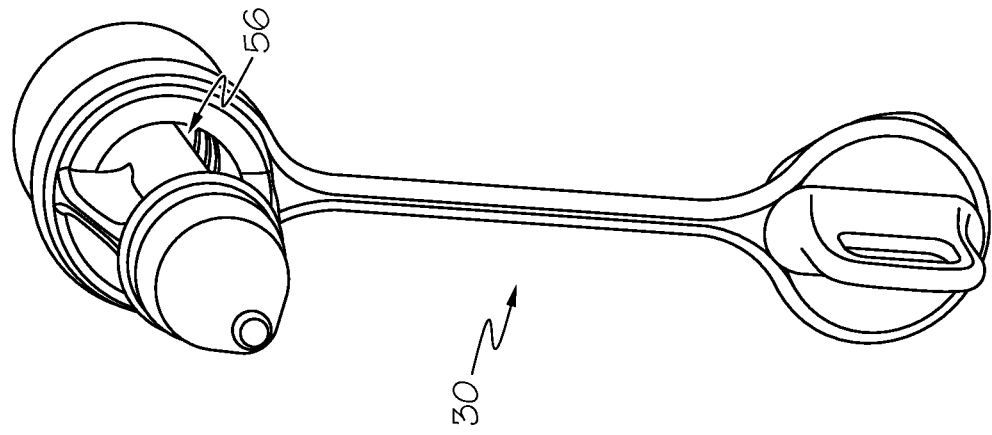
FIG. 5 is another rear perspective view of the male connector of FIG. 1.
Figure 4:
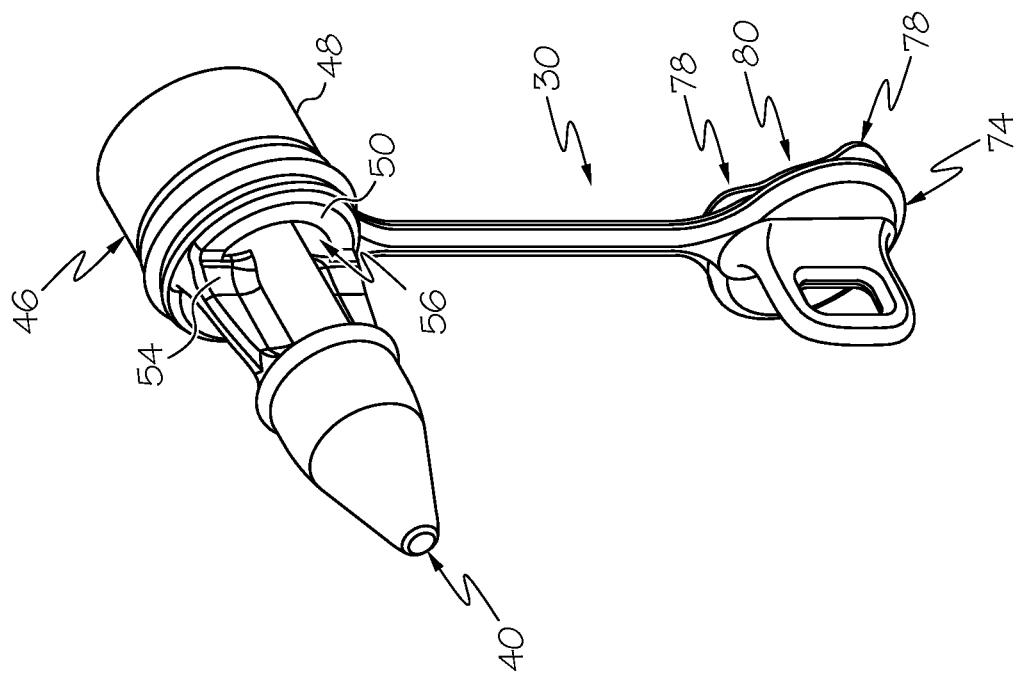
FIG. 4 is a rear perspective view of the male connector of FIG. 1.
Figure 7:
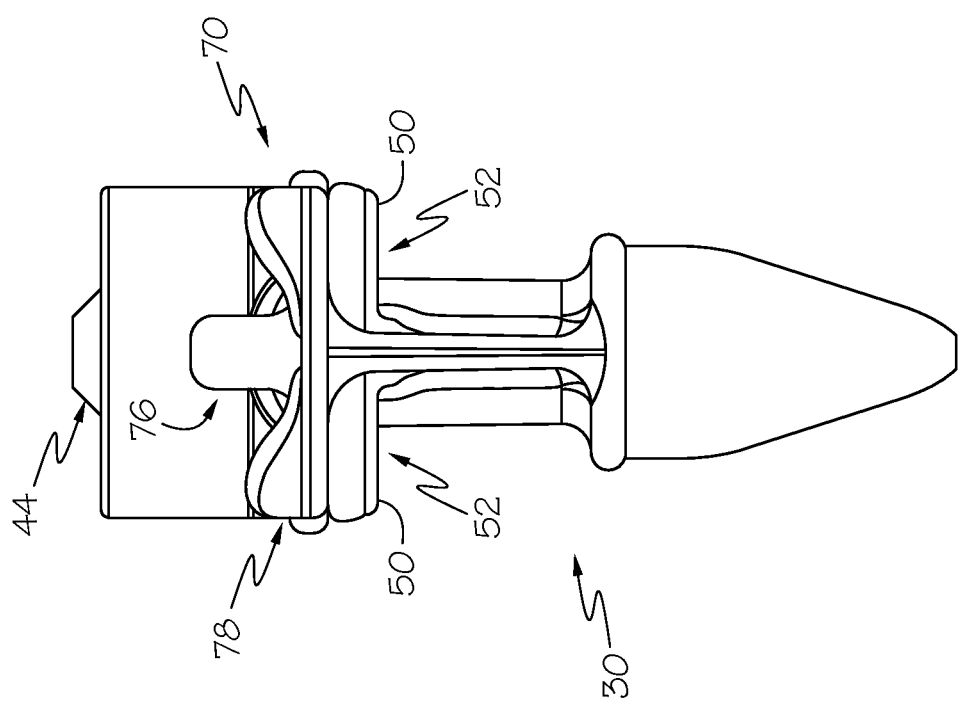
FIG. 7 is another side view of the male connector of FIG. 1.
Figure 6:
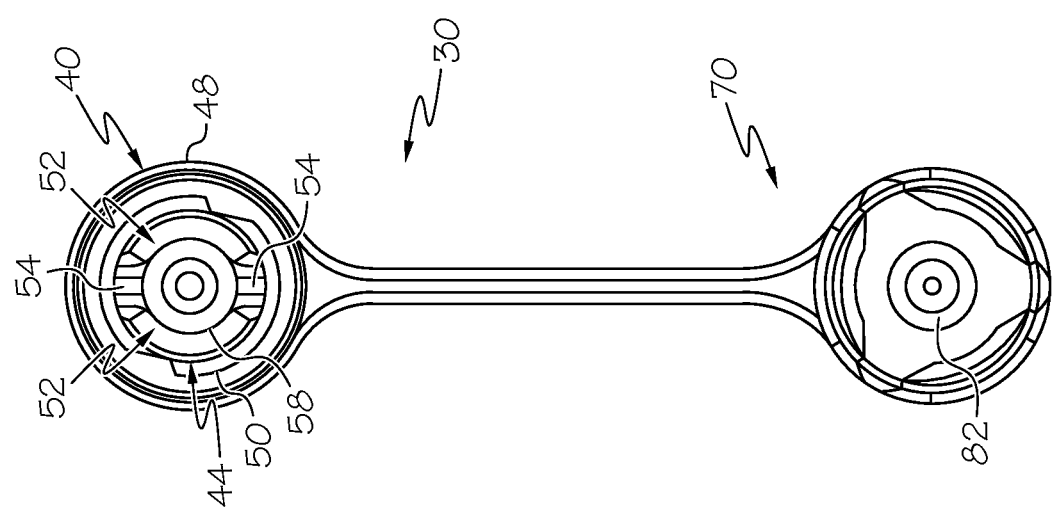
FIG. 6 is a front view of the male connector of FIG. 1.
Figure 8:
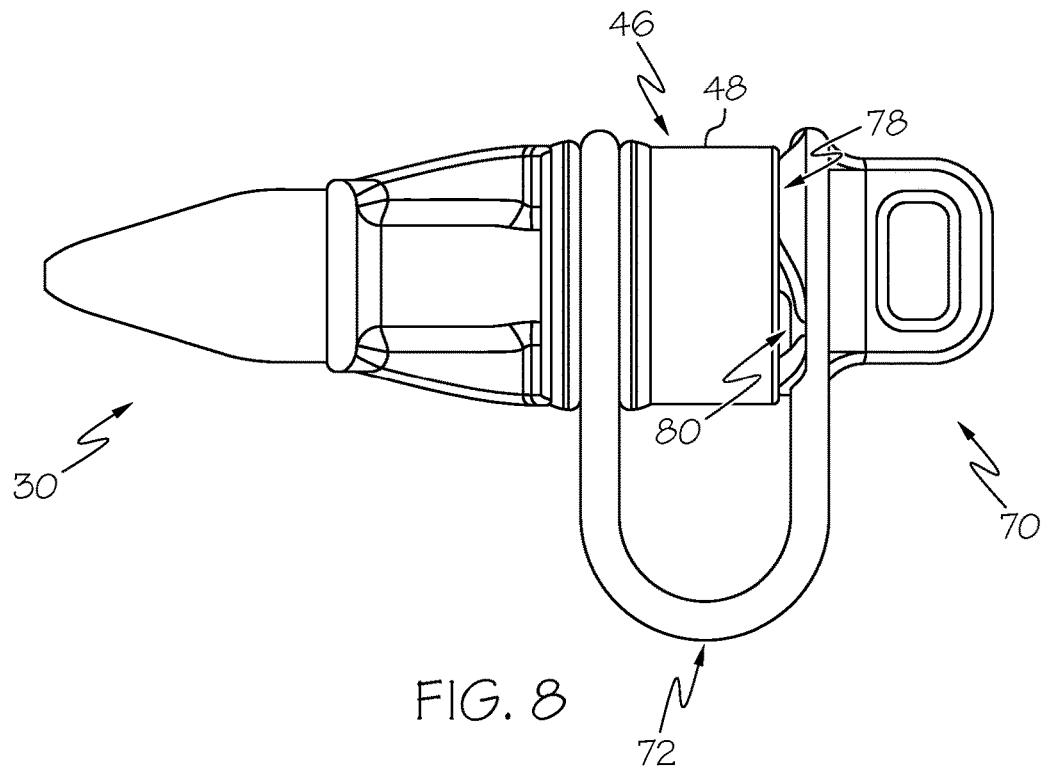
FIG. 8 shows the male connector of FIG. 1 with its cap in a plugged position.
Figure 9:
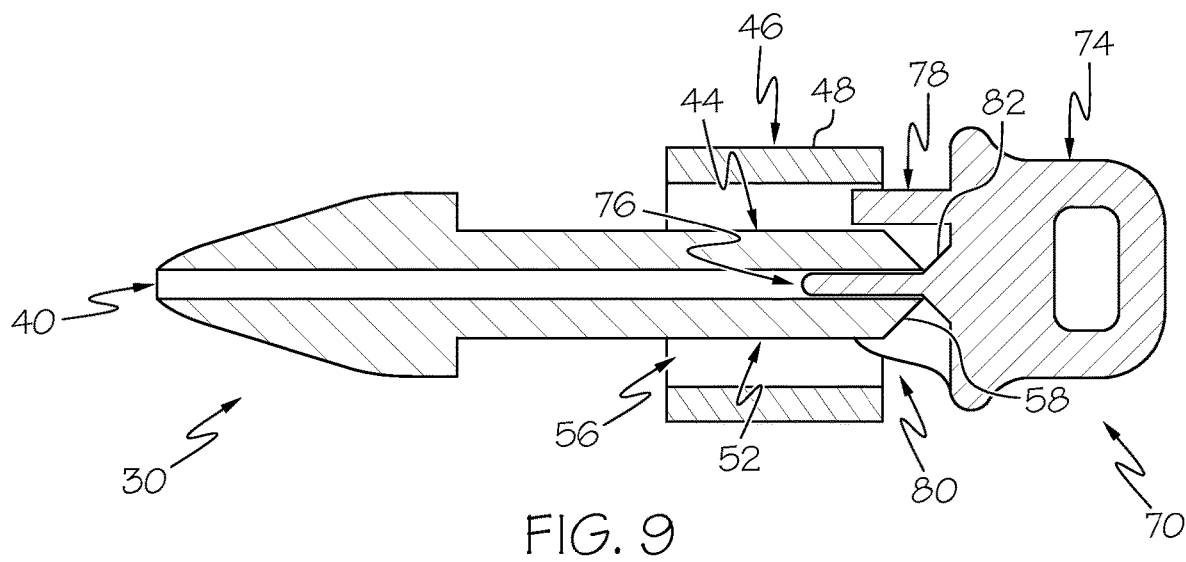
FIG. 9 is a cross-sectional view of the male connector of FIG. 8 showing a ventilation passageway for airflow through the connector with its cap in a plugged position.

The present invention may be understood more readily by reference to the following detailed description taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-9 show a vented connector 30 according to a first example embodiment of the invention. The connector 30 attaches to a medical fluid vessel 10 and mates with a cooperating connector 20 attached to an inline medical fluid vessel 12, with the connectors collectively forming a connector-set or coupling that detachably couples the vessels together for fluid flow therethrough. The connectors 20 and 30 can be made of conventional materials (e.g., as silicone or polyurethane) by conventional fabrication techniques and equipment (e.g., molding).

In the depicted embodiment, the vented connector 30 is attached to a vessel 10 that is a tube, though the term "vessel" is intended to be broadly construed to include any carrier or container for a fluid as well as any fluid-delivery device, and as such in other embodiments the vessel is a catheter, hose, bottle, bag, syringe, pump, or the like. As such, the connectors 20 and 30 can be used to couple together two vessels (with one vessel in/at the patient and the other vessel connected to an upstream medical fluid-delivery device such as a syringe) or to couple one vessel to a medical device (with one vessel in/at the patient and the other vessel being or a part of an upstream medical fluid-delivery device such as a syringe). In the depicted embodiment, the vented connector 30 is used for a vessel 10 for enteral feeding, with the term "vessel" in the "enteral feeding" context intended to be broadly construed to include not just feeding bags but also breast pumps, food bottles, other food-storage containers, extension sets, and the like. In the depicted embodiment, the vented connector 30 is an ENFIT connector for enteral feeding tubes, though in other embodiments the innovative features are included in connectors for fluid vessels for non-enteral and/or non-small-bore (medical or other) applications. And in the depicted embodiment, the vented connector 30 is a male connector and the cooperating connector 20 is a mating female connector, though in other embodiments this is reversed to provide a vented and/or capped female connector with an outer housing defining an annular space. In addition, the vented connector 30 is described herein for use with fluids, which as used herein means liquids and gases.

The connector 30 includes a vessel-attaching portion 32 defining a rear end 34, a coupling-attaching portion 36 defining a front end 38, and a lumen 40 extending longitudinally therethrough from end to end. The vessel-attaching portion 32 attaches to (e.g., receives and secures) the vessel 10 and secures it in place with a good seal by conventional structures such as crimps or adhesives so that the vessel extends longitudinally from the rear end 34. The coupling-attaching portion 36 and the cooperating connector 20 detachably couple together mechanically by mating attachment fittings such as the depicted screw threads 42 and 22 (of the connector 30 and the cooperating connector 20, respectively) or other conventional mating mechanical fasteners as are known to persons of ordinary skill in the art such as bayonet fitting, snap-fit couplings, and the like. And the coupling-attaching portion 36 and the cooperating connector 20 sealingly mate together for fluid conveyance by mating male and female fittings such as the depicted male plug 44 and female receptacle 24 (of the connector 30 and the cooperating connector 20, respectively) or other conventional fluid-sealing structures as are known to persons of ordinary skill in the art such other friction fittings. In the depicted embodiment, the male plug 44 includes a peripheral wall that defines the lumen 40 extending axially all the way through it to convey the fluid through the connector 30. In some embodiments, the mating male and female seal fittings are designed to provide sufficient mechanical/frictional retention forces that the connectors 30 and 20 are securely coupled together and the connectors 30 and 20 thus do not include any separate screw threading or other mechanical fasteners.

In addition, the connector 30 includes an outer housing 46 surrounding its plug 44, for example including a peripheral sidewall 48 and an endwall 50. The outer-housing sidewall 48 is arranged coaxially with and surrounding the plug 44 thereby forming an annular space 52 therebetween with an access opening at the front end 38 of the connector 30 (opposite the endwall). In this way, when the two connectors are coupled together with the male plug 44 of the connector 30 inserted into the female receptacle 24 of the cooperating connector 20, the peripheral sidewall or barrel 26 (defining the receptacle 24) of the cooperating connector 20 is coaxially received in the annular space 52 (between the outer-housing peripheral sidewall 48 and the plug 44) of the connector 30. And the connectors 30 and 20 can be coupled together by the screw threads 42 being inner threads on the outer-housing sidewall 48 and the mating threads 22 being outer threads on the receptacle sidewall 26, by mating threads between the plug and the receptacle sidewall, or by other threading arrangements. The outer-housing sidewall 48 of the connector 30 and the receptacle sidewall 26 of the cooperating connector 20 are typically generally cylindrical in shape and solid in structure (i.e., not fluid permeable).

The outer-housing endwall 50 extends at least partially between the outer-housing sidewall 48 and the plug 44, with at least one (e.g., two, as depicted) connecting portion 54 extending inwardly from the outer-housing sidewall to fix the outer-housing sidewall relative to the plug and thereby form the annular space 52. Typically each connecting portion 54 extends all the way between (e.g., radially, as depicted) and fixes together the outer-housing sidewall 48 and the plug 44. To provide for fluid drainage and airflow ventilation, the outer-housing endwall 50 of the connector 30 includes at least one (e.g., two, as depicted) vent openings 56 providing fluid communication between the annular space 52 and external to the annular space. The connector vent openings 56 can be in the form of two curved slots extending between two connecting portions 54 in the form of radial spokes, as depicted. Alternatively, the connector vent openings can be in the form of ports (e.g., holes in a circular, polygonal, frusto-conical, or other regular or irregular shape) extending axially through the endwall and/or radially through the outer sidewall, mesh openings in an endwall that is a mesh (e.g., a screen, grate, or lattice), or other types and arrangements of openings that provide for fluid drainage and airflow ventilation for the annular space. In addition, the outer-housing endwall 50 has an inner surface (partially defining the annular space 52) that can be sloped (ramped or taper, all or only part of it) toward the connector vent openings 56 to help direct fluid toward them.

In this way, any residual fluid from the vessels 10 and 12 that might otherwise be retained in the annular space 52 resulting in bacteria colonization will instead tend to drain out through the connector vent openings 56 and be dried by airflow in and/or out of the vent openings. Furthermore, the connector vent openings 56 in the outer-housing endwall 50 provide better access to the annular space 52 for inspection and cleaning. Moreover, when the connector 30 is disconnected from the cooperating connector 20, a vacuum can form in the lumen 40 and induce a backflow of the fluid into the connector 30 and/or the cooperating connector 20, resulting in dosing inaccuracies, and the connector vent openings 56 can function to assist in breaking the vacuum to prevent fluid backflow and thus provide for more accurate dosing.

In addition, the connector 30 optionally includes a sanitary cap 70 for the lumen 40 at its front end 38 (opposite the attachment of the vessel 10). The cap 70 can be attached to the connector 30 by a tether 72 such as an integral length of material (as shown) or a cord, string, band, chain, or the like. In addition, the cap 70 can include a handle 73 for gripping to move the cap between its unplugged (see FIGS. 1-7) and plugged positions (see FIGS. 8-9). In the plugged position the cap 70 seals off the lumen 40 and the vessel 10 from outside contamination, which can be advantageous for example in enteral feeding applications in which the vessel 10 is inserted into the patient and left there for future feedings.

The cap 70 includes a body or endwall 74 with a seal fitting (e.g., a plug) 76 and a peripheral sidewall 78 axially extending from it. The cap body/endwall 74 is typically a solid member such as a panel for sealing the annular space when capped. And the cap sidewall 78 can be a solid peripheral member such as a collar or flange, or two or more peripherally arranged prongs such as fingers or tabs, for reception and retention in the annular space when capped. In the plugged position, the cap plug 76 is received in the connector-plug lumen 40 at its front end 38 with a snug fit for sealing to prevent the escape of fluids from the vessel 10. And the cap sidewall 78 is received in the annular space 52 through its access opening so that it engages the connector 30 with a snug fit for mechanical/frictional retention to removably secure the cap 70 in place in the plugged position. In other embodiments, the cap seal fitting is a sleeve, recess, or other structural element that mates with the connector seal fitting to seal the lumen closed. And in yet other embodiments, the cap 70 and the connector 30 additionally or alternatively include mating screw threads or other fasteners for removably securing the parts together.

To provide for fluid drainage and airflow ventilation of the annular space 52 when the cap 70 is the plugged position, the cap includes at least one (e.g., three, as depicted) vent openings 80 providing fluid communication between the annular space and external to the annular space. The cap vent openings 80 can be in the form of one or more notches defined by gaps between one or more segments of the cap sidewall 78, for example the three curved notches between the three segments of the cap sidewall formed by the undulating edge of the cap sidewall, as depicted. Alternatively, the cap vent openings can be in the form of ports (e.g., holes in a circular, polygonal, conical, or other regular or irregular shape) extending axially through the cap body/endwall and/or radially through the cap sidewall, mesh openings in a portion of the cap body that is a mesh (e.g., a screen, grate, or lattice), or other types and arrangements of openings that provide for fluid drainage and airflow ventilation for the annular space with the cap in the plugged position.

In this way, any residual fluid from the vessels 10 and 12 that might otherwise be retained in the annular space 52 (upon disconnection of the connectors 30 and 20) resulting in bacteria colonization will instead tend to drain out through the cap vent openings 80 and be dried by airflow in and/or out of the vent openings. Furthermore, the cap vent openings 80 can facilitate better inspection and cleaning of the annular space 52. Moreover, the connector vent openings 56 and the cap vent openings 80, in combination with the annular space 52, form a continuous passageway (see FIG. 9) for airflow to enter the annular space at one end and exit the other end for enhanced drying and to prevent an airlock that might restrict airflow in and out of the annular space. As such, as used herein reference to connector outer-housing vent openings being "at the outer-housing endwall" includes the vent opening being formed in or by the outer-housing endwall 50 as well as being formed in or by the outer-housing sidewall 48 but immediately adjacent the outer-housing endwall to provide the continuous airflow passageway along substantially the entire length of the annular space 52.

In addition, to make sure that the cap vent openings 80 are at least partially exposed and uncovered (sufficiently for functioning for their intended purpose as described herein) when the cap 70 is in the plugged position on the connector 30, engaging stop surfaces 58 and 82 can be provided on the connector and the cap, respectively, to define (and thus limit) the how far the cap fits onto the connector. In the depicted embodiment, for example, the connector stop surface 58 is formed by a rim of the connector plug 44 defining the lumen 40, and the cap stop surface 82 is formed by a base of the cap plug 76. As can be seen for example in FIGS. 8-9, in the plugged position the cap vent openings 80 are partially covered but still partially exposed to permit fluid flow therethrough. Alternatively, the connector and cap stop surfaces can be formed by at least one inward-extending member (e.g., a collar, flange, rib, tab, or the like) of the outer-housing sidewall and by the rear (insertion) ends of the cap sidewall segments, respectively, so the inward-extending members limit how far into the annular space the cap sidewall segments can be inserted. Further alternatively, the connector stop surface can be in the form of an endwall, collar, flange, rib, tab, or the like on or adjacent the connector plug and/or lumen (e.g., within the lumen), and/or the cap stop surface can be in the form of a skirt, collar, flange, rib, tab, wing, or the like on or adjacent the cap plug.

It should be noted that the depicted embodiment includes the connector vent openings 56 and the cap vent openings 80 in combination, while other embodiments include only one of these two features. Furthermore, it should be noted that some embodiments include connector vent openings in the outer-housing sidewall as an addition or alternate to the depicted connector vent openings 56 in the outer-housing endwall 48, while other embodiments include cap vent openings in the cap endwall as an addition or alternate to the depicted cap vent openings 80 in the cap sidewall 78. As such, any of the vent openings disclosed herein can be implemented individually or in any combination with any other vent opening(s) disclosed herein or not disclosed herein.

Figure 10:
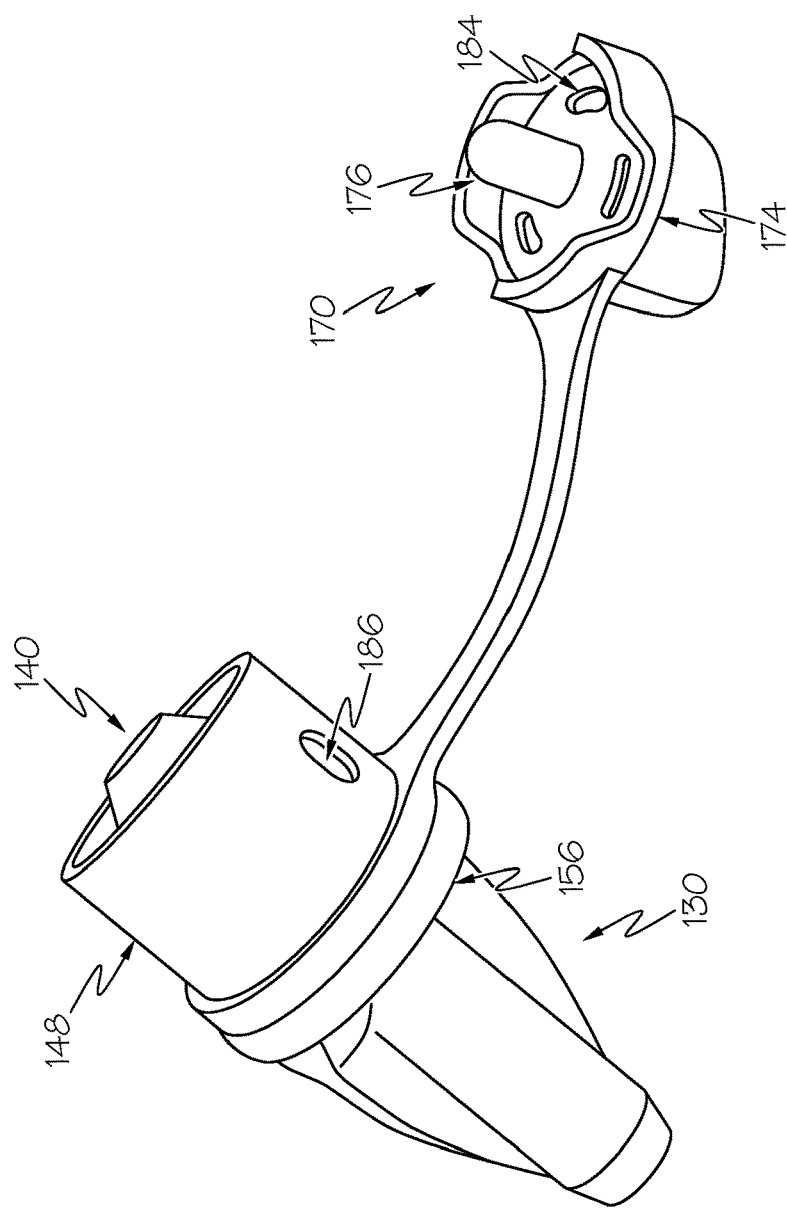
FIG. 10 is a perspective view of a vented connector according to a second example embodiment, shown with its cap unplugged so that it's ready for connection to a mating female connector.

FIG. 10 shows a vented connector 130 according to a second example embodiment of the present invention. The vented connector 130 is substantially similar to that of the first example embodiment described above, with exceptions as noted herein. In this embodiment, for example, the connector 130 includes one or more vent openings 186 formed in the outer-housing sidewall 148, in addition to the one or more vent openings 156 formed in the outer-housing endwall (not shown) described above. The connector vent openings 186 in the outer-housing sidewall 148 provide for drainage and drying, vacuum breaking, and enhanced inspection and cleaning similarly to the venting in the first example embodiment.

In the depicted embodiment, the connector vent openings 186 are generally circular in shape, though in other embodiments the vent openings can have an oval, polygonal, conical, or other regular or irregular shape. The depicted connector vent openings 186 are positioned sufficiently away from the front/cooperating connector end of the connector 130 that they are not blocked by the cap sidewall segments when the cap 170 is plugged onto the connector (with the cooperating connector detached). In other embodiments, the vent openings are provided with deflectors (e.g., V-shaped members extending inward from the inner surface of the outer-housing sidewall and positioned between the vent openings and the front end) that are engaged by and induce rotation of the cap sidewall segments when the cap is plugged onto the connector so that the vent openings align with the cap sidewall vent openings. And in still other embodiments, an array or series of the sidewall vent openings are provided.

In addition, the cap 170 can have one or more vent openings 184 axially formed in the cap body or endwall 174. The cap vent openings 184 are positioned radially outward from the cap plug 176 so that when the cap 170 is plugged onto the connector 130 they provide ventilation to the annular space 152 but they do not provide ventilation to the lumen 140. The cap vent openings 184 can be in the form of curved slots (as depicted) or they can have a circular, polygonal, conical, or other regular or irregular shape. In other embodiments, the connector 120 includes only the cap vent openings 184 or only the connector vent openings 186.

Figure 11:
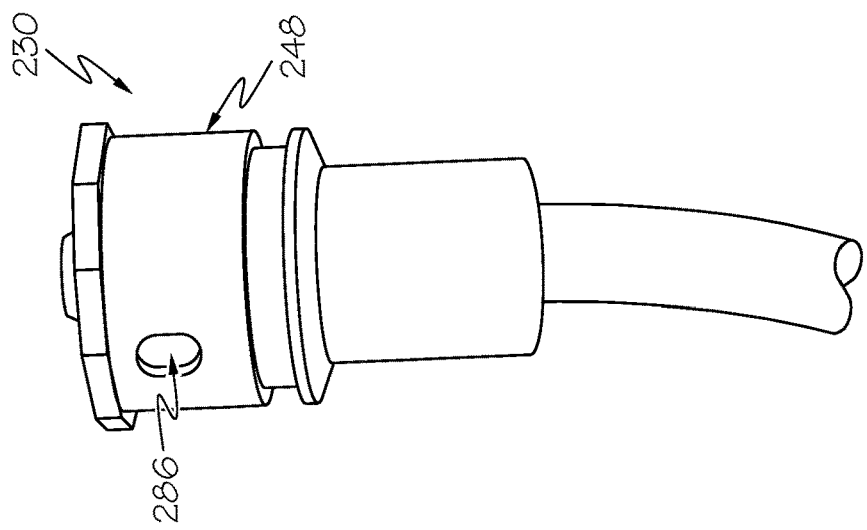
FIG. 11 is a perspective view of a vented connector according to a third example embodiment, shown without its cap.

FIG. 11 shows a vented connector 230 according to a third example embodiment of the present invention. The vented connector 230 is substantially similar to those of the first and second example embodiments described above, with exceptions as noted herein. In this embodiment, for example, the connector 230 includes the one or more vent openings 286 formed in the outer-housing sidewall 248, but not any vent openings formed in the outer-housing endwall. The connector vent openings 286 in the outer-housing sidewall 148 provide for drainage and drying, vacuum breaking, and enhanced inspection and cleaning similarly to the venting in the first and second example embodiments. It should be noted that the connector 230 is depicted without a cap, though in some embodiments a cap is provided, and the cap can include cap vent openings as described herein as an addition or alternate to the connector vent openings 286.

While the invention has been described with reference to preferred and example embodiments, it will be understood by those skilled in the art that a variety of modifications, additions and deletions are within the scope of the invention, as defined by the following claims.

What is claimed is:

1. A male connector for connection to a fluid vessel and a cooperating female connector, the cooperating female connector including a peripheral sidewall that defines a female receptacle and that includes a mechanical fastener, the male connector comprising:
    a first end from which the vessel extends, a second end for engaging the cooperating female connector, and a lumen extending therethrough from the first end to the second end;
    a fluid-seal male fitting that at least partially defines the lumen and sealingly mates with the cooperating female connector to provide conveyance of the fluid through the male connector lumen, between the cooperating female connector and the vessel, without any drainage or venting directly from the lumen, wherein the fluid-seal fitting is in the form of a male plug that is received by the cooperating female connector female receptacle, wherein the male plug comprises a fixed end proximal to the first end and a free end extending toward the second end; and
    an outer housing positioned peripherally around the male plug to form an annular space therebetween with an access opening at the second end of the male connector, wherein the outer housing includes a peripheral sidewall and an endwall that cooperate with the male plug to define the annular space, the endwall is positioned opposite the access opening with the outer housing peripheral sidewall therebetween, the male connector annular space at least partially receives the cooperating female connector peripheral sidewall through the annular space access opening, and the outer housing peripheral sidewall includes a mechanical fastener that mechanically couples with the cooperating female connector mechanical fastener, wherein the annular space at the second end of the male connector is defined between the outer housing and the free end of the male plug for receiving the cooperating female connector therein,
    wherein the outer housing includes at least one vent opening extending between the annular space and external to the annular space and formed in the endwall of the outer housing, wherein the at least one vent opening allows for drainage and air-drying, through the endwall, of any residual amount of the fluid in the annular space, but not in the lumen, when the male connector is disconnected from the cooperating female connector and the access opening of the annular space is capped, further wherein the outer housing includes one or more connecting portions extending inward continuously from the outer housing peripheral sidewall to the fluid-seal male fitting and extending along the fluid-seal male fitting from the outer housing endwall toward the first end.

2. The male connector of claim 1, further comprising at least one vent opening formed in the outer housing peripheral sidewall.

3. The male connector of claim 1, wherein the one or more connecting portions define the at least one vent opening formed in the outer housing endwall.

4. The male connector of claim 1, wherein the at least one vent opening formed in the outer housing endwall is in the form of a curved slot.

5. The male connector of claim 1, wherein the at least one vent opening formed in the outer housing endwall, assists in breaking a vacuum created within the male connector lumen to prevent fluid backflow and thereby reduce dosing inaccuracies.

6. The male connector of claim 1, wherein the cooperating female connector mechanical fastener includes a screw thread, and wherein the outer housing mechanical fastener includes a screw thread that mates therewith when the cooperating female connector peripheral sidewall is received in the male connector annular space between the outer housing peripheral sidewall and the fluid-seal fitting.

7. The male connector of claim 1, wherein the male connector is adapted for use for enteral feeding.

8. A male connector for connection to a vessel for a medical fluid and to a cooperating female connector, the male connector comprising:
a first end from which the medical-fluid vessel extends, a second end, and a lumen extending therethrough from the first end to the second end;
a male plug that at least partially defines the lumen and sealingly mates with a female receptacle defined by a peripheral sidewall of the cooperating female connector to provide conveyance of the medical fluid through the lumen between the cooperating female connector and the vessel without any drainage or venting directly from the lumen, wherein the male plug comprises a fixed end proximal to the first end and a free end extending toward the second end;
an outer housing coaxially arranged around the male plug to form an annular space therebetween with an access opening at the second end of the male connector, the outer housing including a peripheral sidewall and an endwall that cooperate with the male plug to define the annular space, the annular space at least partially receiving the cooperating female connector sidewall when the male connector and cooperating female connector are coupled together, and the outer housing including one or more vent openings at the outer housing endwall and extending between the annular space and external to the annular space, wherein the annular space at the second end of the male connector is defined between the outer housing and the free end of the male plug for receiving the cooperating female connector therein;
wherein the one or more vent openings allow for drainage and air-drying, through the endwall, of any residual amount of the medical fluid in the annular space but not in the lumen, and wherein the one or more vent openings in combination with the annular space and the access opening form a continuous passageway allowing airflow to enter the annular space at one end through the annular space access opening and exit an opposite end through the one or more vent openings for enhanced drying; and
wherein the outer housing further comprises one or more connecting portions extending continuously radially between the outer housing peripheral sidewall and the male plug and extending along the male plug from the outer housing endwall toward the first end.

9. A connector-set including the male connector in combination with the cooperating female connector of claim 8.

10. The male connector of claim 8, further comprising a cap repositionable between a plugged position capping the male connector second end and an unplugged position not capping the male connector second end, the cap including an endwall and a fluid-seal fitting that sealingly mates with the lumen in the plugged position, and the cap including one or more vent openings extending between the annular space and external to the annular space when the cap is in the plugged position capping the access opening of the annular space.

11. The male connector of claim 10, wherein the cap further includes a peripheral sidewall that extends from the endwall and engages the male connector in the plugged position, wherein the one or more cap vent openings include at least one cap vent opening formed in the cap sidewall, the cap sidewall is at least partially received in the male connector annular space when the cap is in the plugged position, and the male connector and the cap include respective mechanical stop surfaces that engage each other to limit travel of the cap sidewall relative to the outer housing and thereby define the plugged position with the at least one cap sidewall vent opening remaining at least partially exposed.

12. The male connector of claim 8, wherein the cooperating female connector further includes a mechanical fastener, and wherein the male connector outer housing peripheral sidewall further includes a mechanical fastener that mechanically couples with the cooperating female connector mechanical fastener.

13. The male connector of claim 8, wherein the one or more connecting portions are in the form of radial spokes.

14. An enteral-feeding male connector for connection to a fluid vessel and a cooperating female connector, the cooperating female connector including a peripheral sidewall that defines a female receptacle and that includes outer screw threads, the male connector comprising:
a first end from which the vessel extends, a second end for engaging the cooperating female connector, and a lumen extending therethrough from the first end to the second end;
a fluid-seal fitting that at least partially defines the lumen and sealingly mates with the cooperating female connector to provide conveyance of fluid through the lumen between the cooperating female connector and the vessel without any drainage or venting directly from the lumen, wherein the fluid-seal fitting is in the form of a male plug that is received by and sealingly mates with the cooperating female connector female receptacle, wherein the male plug comprises a fixed end proximal to the first end and a free end extending toward the second end; and
an outer housing positioned around the male plug to form an annular space therebetween with an access opening at the second end of the male connector, wherein the outer housing includes a peripheral sidewall and an endwall that cooperate with the male plug to define the annular space, the outer housing peripheral sidewall extends from the access opening toward the first end of the male connector, the endwall is positioned opposite the access opening with the outer housing peripheral sidewall therebetween, the annular space at least partially receives the cooperating female connector sidewall through the annular space access opening, and the outer housing peripheral sidewall includes inner screw threads that mechanically couple with the cooperating female connector outer screw threads, wherein the annular space at the second end of the male connector is defined between the outer housing and the free end of the male plug for receiving the cooperating female connector therein, and wherein the outer housing includes at least one vent opening extending between the annular space and external to the annular space and formed in the endwall opposite the access opening, and the outer housing includes two connecting portions that each extend radially between the outer housing peripheral sidewall and the male plug and each extend along the male plug from the endwall toward the fixed end to at least partially define the at least one vent opening, wherein the at least one vent opening allows for drainage and air-drying, through the endwall, of any residual amount of the fluid in the annular space, but not in the lumen, when the male connector is disconnected from the cooperating female connector and the access opening of the annular space is capped.

15. The male connector of claim 14, wherein the at least one vent opening further includes at least one vent opening formed in the sidewall.

16. The male connector of claim 14, further comprising a cap repositionable between a plugged position capping the male connector second end and an unplugged position not capping the male connector second end, the cap including an endwall and a fluid-seal fitting that sealingly mates with the lumen in the plugged position, and the cap including one or more vent openings extending between the annular space and external to the annular space when the cap is in the plugged position capping the access opening of the annular space.

17. A connector-set including, in combination, the male connector and the cooperating female connector of claim 14.

\* \* \* \* \*